United States Patent [19]

Powell et al.

[11] Patent Number: 5,100,580

[45] Date of Patent: Mar. 31, 1992

[54] PHOSPHORESCENT MATERIALS

[75] Inventors: David C. Powell, Tunbridge Wells; Aubrey D. Walker, North Harrow, both of England

[73] Assignee: The Post Office, of Postal Headquarters, London, United Kingdom

[21] Appl. No.: 719,676

[22] Filed: Jun. 24, 1991

Related U.S. Application Data

[63] Continuation of Ser. No. 478,070, Feb. 7, 1990, abandoned, which is a continuation of Ser. No. 154,937, Feb. 11, 1988, abandoned.

[51] Int. Cl.$^5$ .............................................. C09K 11/02
[52] U.S. Cl. .................................................. 252/301.35
[58] Field of Search .................................... 252/301.35

[56] References Cited

U.S. PATENT DOCUMENTS

| | | | |
|---|---|---|---|
| 3,744,877 | 7/1973 | Stamm | 252/301.35 |
| 3,867,302 | 2/1975 | Takano et al. | 252/301.34 |
| 4,022,709 | 5/1977 | Ferro et al. | 252/301.35 |
| 4,089,995 | 5/1978 | Ferro et al. | 427/157 |
| 4,201,808 | 5/1980 | Cully et al. | 427/54.1 |
| 4,500,116 | 2/1985 | Ferro et al. | 428/530 |
| 4,637,988 | 1/1987 | Hinshaw et al. | 252/301.35 |
| 4,647,400 | 3/1987 | Dubroca et al. | 252/301.35 |

FOREIGN PATENT DOCUMENTS

| | | |
|---|---|---|
| 870504 | 6/1961 | United Kingdom . |
| 1146522 | 3/1969 | United Kingdom . |
| 1494102 | 12/1977 | United Kingdom . |
| 1494103 | 12/1977 | United Kingdom . |
| 2016370 | 3/1979 | United Kingdom . |

Primary Examiner—John Niebling
Assistant Examiner—Steven P. Marquis
Attorney, Agent, or Firm—Merchant, Gould, Smith, Edell, Welter & Schmidt

[57] ABSTRACT

An organic phosphor which is a solid insoluble in water and organic solvents and which may be used in a phosphorescent printing ink or a paper coating composition comprises molecules of at least one phosphorescent activator held within a matrix of a condensation resin that does not itself absorb ultraviolet or visible radiation at the excitation and emission frequencies of the phosphorescence activator(s). The phosphorescence activator(s) is/are a compound or mixtures of compounds of the general formula $$(A)_m\text{—Ar—CO—X} \tag{I}$$

wherein Ar denotes a fused ring polycyclic aromatic group;
  m is zero or an integer of from 1 up to the maximum number of ring positions available for substitution;
  X denotes an alkyl group or a group of the formula $(A)_m$—Ar— or $(B)_n$Ph—wherein Ph is a phenyl group and n is zero or an integer of from 1 to 5; and
  A and B represent ring substituents, or an acid addition salt thereof when said compound is basic.

29 Claims, No Drawings

PHOSPHORESCENT MATERIALS

This is a continuation of application Ser. No. 07/478,070 filed Feb. 7, 1990 now abandoned, which is a continuation of application Ser. No. 07/154,937 filed Feb. 11, 1988, now abandoned.

BACKGROUND TO THE INVENTION

This invention relates to organic phosphors comprising molecules of at least one phosphorescence activator held within a matrix of a condensation resin that does not itself absorb ultra-violet or visible radiation at the excitation and emission frequencies of the phosphorescence activator.

Phosphors of such type are known for example from British Patent Specifications Nos.870,504, 1,494,102 and 1,494,103. Such phosphors may contain as a matrix a cross-linked condensation resin, the resin being formed by condensation in the presence of phorphorescence activators so that the molecules of the latter are trapped and isolated from one another in the matrix. The resin is preferably a condensation product of formaldehyde, generally with an amine group-containing compound, especially urea or melamine. The phosphor is a solid generally insoluble in water and organic solvents and for use as a phosphorescent printing ink may be ground finely and dispersed in a suitable solvent, for example toluene.

The phosphorescence activators which have hitherto been proposed fall within a variety of classes of organic compounds. Examples of such compounds include carbazole sulphonic acid, naphthalene disulphonic acid, diphenyl guanadine and 2-aminobenzoflavone. However the mean intensity of the phosphorescent emission obtained with such compounds is often mediocre for practical use in for example security marking of documents and products.

SUMMARY OF THE INVENTION

It is an object of this invention to provide organic phosphors showing improved phosphorescent behaviour.

According to the present invention there are provided organic phosphors as aforesaid wherein there is present at least one phosphorescence activator which is a compound of the general formula $$(A)_m\text{—Ar—CO—X} \qquad (I)$$

wherein Ar denotes a fused ring polycyclic aromatic group;
m is zero or an integer of from 1 up to the maximum number of ring positions in Ar available for substitution;
X denotes an alkyl group or a group of the formula $(A)_m$—Ar— or $(B)_n$Ph— wherein Ph is a phenyl group and n is zero or an integer of from 1 to 5; and
A and B represent ring substituents; or an acid addition salt thereof when said compound is basic.

In the aforesaid general formula, Ar is preferably an optionally substituted hydrocarbyl group, especially naphthyl, anthryl, phenanthryl, acenaphthyl or acenaphthenyl group. However, it is also possible for a heterocyclic ring to be fused to an aromatic ring which is bonded to the acyl group X—CO— as in a carbazolyl group.

The substituents A and B, if present, may be any one of the following radicals:
alkyl or cycloalkyl—R
phenoxy—O Ph or alkoxy or cycloalkoxy—OR
hydroxy—OH
phenyl—Ph
amino—$NH_2$
amino

carboxyl

(or salt or ester)
sulphonic acid —$SO_3H$ (or salt or ester)
halogeno—F, —Cl, —Br, —I
cyano—CN
azido—$N_3$ or optionally substituted phenylazo i.e. B—pH—N=N
hydrazino—$NHNH_2$
aldehyde—CHO The group A or B may also be a combination of the aforementioned radicals as for example in a tertiary amino group which may have the formula —$NR_3$, a halogenated alkyl group such as —$CF_3$ or a substituted phenyl group.

The compounds of the formula I form a valuable class of substances which are capable of displaying phosphorescence under suitable conditions when incorporated in organic phosphors as aforesaid, in which they are preferably present in an amount of from 0.25 to 10 per cent by weight, based on the total weight of resin and activator.

The aforementioned compounds may be prepared by Friedel Crafts acylation of a polycyclic aromatic hydrocarbon or substituted derivative thereof with the appropriate acid chloride or acid anhydride. The essential reaction is as follows:

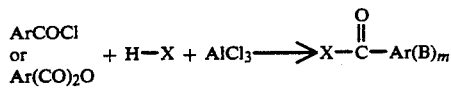

This method is both simple and suitable for commercial development despite the disadvantage of the possibility of forming more than one ketonic substituted isomer. The isomers may be isolated in pure form or for reasons which will be apparent from the foregoing, may be used in admixture in the aforementioned phosphor compositions. In general, herein, where reference is made to the structure of a specific isomer, unless otherwise indicated this will indicate the major isomer predicted ior the Friedel Crafts reaction utilised in a specific comparative procedure. In general, limited purification of the product has been carried out followed by chromatographic analysis and the product obtained (found in most cases to be 90% pure) was utilised in subsequent tests.

In practice, the selection of starting reactants will depend upon the reaction conditions to be employed and the use of the desired product. Thus having regard to the Friedel Crafts reaction, it has been found that naphthalene and phenanthrene give good results. It would also be expected that anthracene, being another simple fused hydrocarbon would give similar results. Having regard to the intended use of the phosphors including the compounds in printing inks, substitution of the groups Ar and X may be provided to render the compounds of formula I soluble in the solvent of the ink. This may be provided by substitution in the starting compounds or by substitution of the product of the Friedel Crafts reaction. In the latter case, it is possible that there may be produced a mixture of compounds depending upon the course of substitution and again, it may be more convenient to utilise such mixtures of compounds in the aforementioned phosphor compositions. A particularly preferred type of substitution in this respect is through sulphonation of the Friedel Crafts reaction product.

According to one embodiment of the invention, there is proposed the use of a compound or mixture of compounds of the formula II;

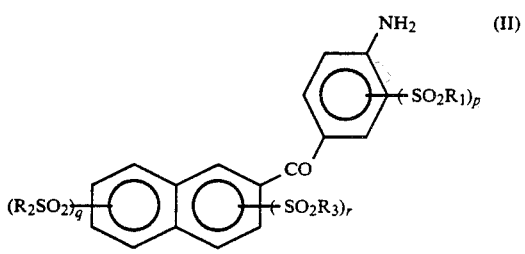

wherein:
each of $R_1$, $R_2$ and $R_3$, which may be the same or different, represents
—OH,
—OM where M represents a monovalent cation or 1/m of an m-valent cation,
a halogen atom, or
—OR where R represents an unsubstituted or substituted alkyl, aryl or cycloalkyl radial,
p represents O or an integer from 1 to 4,
q represents O or an integer from 1 to 4,
r represents O or an integer from 1 to 3.
The unsulphonated compounds of the formula Ia:

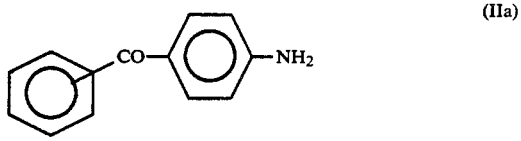

and the free sulphonic acids and their salts of the formula IIb

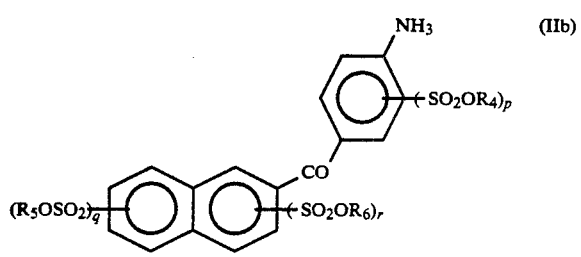

wherein each of $R_4$, $R_5$ and $R_6$, which may be the same or different, represents H or M, where M is as previously defined, are of especial interest. These compounds and mixtures thereof are capable of displaying high-intensity phosphorescence under suitable conditions, producing a brilliant yellow-green afterglow.

The production of compounds used in phosphors embodying this invention will now be described in greater detail with reference to the compounds of formulae(II), (IIa) and (IIb), but it should be appreciated that analogous reaction procedures may be employed to produce any compound of the present invention in accordance with the nature of radicals Ar X and A.

Insofar as the Friedel Crafts reaction for acylating the nucleus of a polycyclic aromatic compound is concerned, particularly in producing compounds of general formula IIa, this may be carried out by the Friedel-Crafts acylation of naphthalene with a p-nitrobenzoyl halide, for example, the chloride. followed by reduction of the nitro group to an amino group. The first stage may be carried out using an aluminium chloride catalyst in an inert solvent such as carbon disulphide, and the second, reduction, stage may be effected, for example, by means of stannous chloride in the presence of hydrochloric acid; the reaction scheme may be represented as follows:

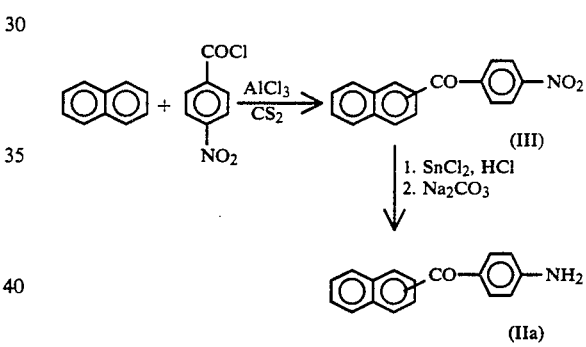

The first stage of this reaction scheme give a mixture of α- and β-substituted products of the formula III, the proportions depending on the temperature and duration of the reaction The second stage is indicative of reactions which may be carried out to modify substituents already present in the product of the Friedel Crafts reaction. The second stage does not alter the distribution of the isomers. The subsequent sulphonation reaction yields a mixture of products of different degrees of sulphonation. The number and position of the sulphonic acid groups or of sulphonic acid derivative groups does not appear to be relevant to the phosphorescence property and the mixture of products obtained by the sulphonation process may be used as a phosphor without there being any necessity for separation. It is believed that the mixed sulphonated product has on average 2 to 3 sulphonic acid groups or sulphonic acid derivative groups per molecule.

This procedure, with the exclusion of a reduction reaction using stannous chloride, that is a reaction scheme wherein a Friedel Crafts reaction is followed by sulphonation, has also been utilised to produce sulphonated benzoyl naphthalene of formula:

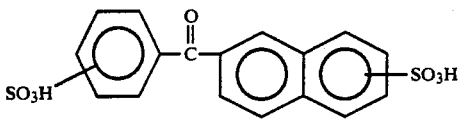

and also sulphonated naphthoylnapthalene of the formula:

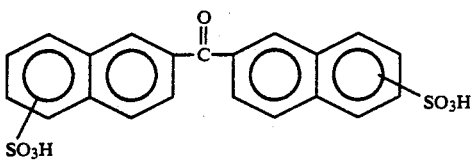

However as will be apparent from the foregoing, the present invention is not limited to the sulphonated compounds and other compounds having the character of phosphorescence activators for use in organic phosphors according to the invention which have been produced are the following:
3-(4-aminobenzoyl)phenanthrene
3-(4-methoxybenzoyl)phenanthrene
3-benzoylphenanthrene
3-acetylphenanthrene
3-(2-carboxybenzoyl)phenanthrene
3-(1-carboxynaphth-8-oyl)phenanthrene
3-(4-aminobenzoyl)carbazole
2-(4-aminobenzoyl)naphthalene
2-(4-aminobenzoyl)anthracene
3-(4-aminobenzoyl)acenaphthylene
2-(4-methoxybenzoyl)naphthalene
2-(4-hydroxybenzoyl)naphthalene
2-(4-carboxybenzoyl)naphthalene
2-(2-carboxybenzoyl)naphthalene
2-(4-chlorobenzoyl)naphthalene
2-(4-n-butylbenzoyl)naphthalene
2-(4-azidobenzoyl)naphthalene
2-(4-hydrazinobenzoyl)naphthalene
2-[4-(4-hydroxyphenylazo)-benzoyl]naphthalene
2-(naphth-2-oyl)-naphthalene
2-(naphth-2-oyl)phenanthrene Phosphors of the present invention will, under suitable conditions, exhibit intense phosphorescence during and after irradiation with ultra violet light. In practice either long-wavelength UV (365 nm) or short-wavelength UV (254 nm) is generally used to induce phosphorescence and the phosphors of the invention show a good response to both. The phosphorescence represents the radiative decay of a triplet excited state to the singlet ground state; this transition is forbidden and the triplet state has a relatively long lifetime, so that afterglow occurs. Collision-induced non-radiative decay pathways are more favourable and will always predominate under conditions in which molecular interaction is possible, for example, in the liquid phase. To obtain observable phosphorescence it is necessary to prevent non-radiative decay by isolating the molecules from one another in a rigid matrix. The matrix itself must, of course, be reasonably transparent to radiation at the absorption and emission frequencies of the phoshporescent molecule, which is generally referred to in this context as the phosphorescence activator.

The organic phosphors of the present invention will generally be produced by methods known per se but utilising the phosphorescence activators which, according to the present invention, have been found to be particularly suitable for use therein. Thus, one form of matrix which may be used successfully in connection with prior art phosphorescence activators, and is claimed, in British Patent Specifications 870,504, 1,494,102 and 1,494,103.

The resin is preferably a condensation product of formaldehyde, more preferably with an amino compound, especially urea or melamine, and is advantageously as described in any of the three British patent specifications mentioned above.

A phosphor embodying this invention is a solid insoluble in water and organic solvents, and for use as a phosphorescent printing ink may be ground finely and dispersed in a suitable solvent, for example, toluene.

The phosphor may, for example, be in the form of printed matter on a substrate, especially paper or plastics material, or in the form of a coating on paper. As a further possibility encompassed by the invention, the condensation resin of such a phosphor may have been formed in situ on the substrate. An ink or coating of this type is described and claimed in British Patent Specification No. 1,494,102, and the in situ condensation process is carried out as described and claimed in British Patent Specification No. 1 494 103. Such an ink or coating which acts as a precursor for the organic phosphor of this invention comprises, in an aqueous solution, at least one phosphorescence activator which is a compound of such type essentially for use in the present invention and which is water soluble and further comprises as solute a soluble precondensate obtained by a reaction between two or more components, the soluble precondensate being capable of further reaction in the absence of the phosphorescence activator(s) to form an insoluble condensation product that does not substantially absorb ultraviolet radiation at any wavelength at which the phosphorescence activator(s) substantially absorb. ultraviolet radiation and which is capable of such further reaction in the presence of the phosphorescence activator(s) to form a phosphorescent insoluble condensation product.

An especially advantageous effect may be obtained if the phosphorescence activator of the invention is used in conjunction with another activator the emission of which is of different wavelength and of different duration. The observed afterglow then appears to change colour with time; moreover the presence of two different emission frequencies may be detected with suitable apparatus and the response of the phosphor to long-wavelength (365 nm) UV and short-wavelengths (254 nm) UV may also be different, if one of the two activators is activated only by short-wavelength UV.

One activator, already known per se, which is especially suitable for use in conjunction with the activator of the present invention is carbazole sulphonic acid, either as the free acid or in the form of a salt. for example, the sodium salt. This activator produces a blue afterglow of a longer duration than that of the afterglow of the activator of the invention. The afterglow of a phosphor containing both activators thus changes from yellow-green to blue over a period of a few seconds. The weight ratio of the phosphorescence activator used essentially according to this invention to such a carbazole sulphonic acid is preferably within the range 0.2 to 1.0, based on the sodium salts of the two activators.

The following Examples illustrate the invention.

EXAMPLE 1

Preparation of p-aminobenzoyl naphthalene (formula IIa)

Naphthalene (1500 g) and p-nitrobenzoyl chloride (1800 g) were dissolved in carbon disulphide (8 liters) in a 20-liter flask. The flask was fitted with a mercury sealed stirrer, reflux condenser, and from the reflux condenser an HCl gas absorption device.

Anhydrous aluminium chloride powder (1400 g) was added in small portions with stirring, over 2 hours. HCl was evolved and a dark brown granular product separated. The reactants were allowed to stand for 24 hours and the product filtered off. The dark brown product was washed with petroleum spirit (40/60) (about 2 liters) and air-dried. It was then added cautiously to crushed ice (5 kg), concentrated HCl (2 liters) and water (10 liters) until hydrolysis of the aluminium chloride complex was complete. The product was filtered off and air-dried.

Stannous chloride (7 kg) was dissolved, with warming, in concentrated HCl (8 liters) and the product from above added, with warming, in small portions. Since the reaction is strongly exothermic, the product was added at such a rate as to control the reaction (boiling gently). The mixture was then left to stand for 24 hours and a brown solid separated which was filtered off and air-dried.

The product, as the stannic chloride complex, was dissolved in a minimum volume of warm acetone. Solid anhydrous sodium carbonate was then added until effervescence ceased (water being added to speed up the reaction). The dark acetone solution was filtered through kieselguhr, and a small volume of water added until precipitation commenced.

The filtrate was then boiled for 10 mins with decolourising charcoal. The charcoal was filtered off and the product precipitated, as a dark red oil, with excess water. When the oil had solidified, it was recrystallised from a minimum volume of boiling methanol (this solution was also decolourised with charcoal). The yellow product which crystallised from methanol was filtered off and thoroughly dried; the yield was about 1 kg. This product was suitable for use as a phosphorescence activiator without further purification.

EXAMPLE 2

Sulphonation of p-aminobenzoyl naphthalene 500 g or one thoroughly dried p-aminobenzoyl naphthalene obtained in Example 1 were powdered and placed in a 5-liter flask. 500 ml of oleum (20% free $SO_3$) were added very cautiously, stirring with a glass rod. The rate of addition of oleum was such that a mobile red syrup was produced with very few fumes. The syrup was then added cautiously to water (about 3 liters). Most of the syrup was water-soluble; a small amount of insoluble by-product was filtered off and discarded.

The aqueous solution of sulphuric acid was then neutralised with NaOH solution. The resulting aqueous liquors were evaporated under reduced pressure to a volume of about 2 liters, cooled and a mass of $Na_2SO_4$ by-product crystallised out which was filtered off. The solution was evaporated further and more $Na_2SO_4$ removed.

The deep brown solution was finally evaporated to dryness, further dried in an oven and ground up. The organic content was determined by combustion, and the product was found to consist of about 60 per cent by weight of p-aminobenzoyl naphthalene sodium sulphonates, the remainder being sodium sulphate. This product was suitable for use as a phosphorescence activator without further purification.

EXAMPLE 3

Preparation of a particulate organic phosphor (a) Urea (5 kg) was melted and heated until it boiled gently. 40 g of the product obtained in Example 2 were added and heating was continued until the molten urea began to be turbid. During the heating stage, decomposition of the urea into various products, chiefly cyanuric acid, was occurring; the onset of turbidity indicated that the solubility of cyanuric acid in urea had been exceeded, and the heating was discontinued at this point.

Paraformaldehyde (1950 g) was added gradually to the reaction mixture with continuous stirring, slight heat being applied when necessary to keep the mixture molten. The fully mixed product was heat-cured at 150° C. for 2 to 4 hours, allowed to cool, and then ground to a fine powder.

(b) The procedure just described was then repeated using the unsulphonated product of Example 1.

EXAMPLE 4

Preparation of a particulate two-component organic phosphor

A particulate organic phosphor containing, as phosphorescence activator, the sodium salt of carbazole sulphonic acid was prepared by a method analogous to that described in Example 3($a$), the 40 g of the product of Example 2 being replaced by 165 g of the sodium salt of carbazole sulphonic acid. After grinding, 1 part by weight of the finely powdered product was thoroughly mixed with 2 parts by weight of the product of Example 3($a$).

EXAMPLE 5

Preparation of a particulate two-component organic phosphor—alterative method

Instead of a physical mixture of two separately prepared phosphors, the two-component phosphor may be a composite product made by carrying out the urea-formaldehyde condensation in the presence of a mixture of the two activators. In this procedure, the methods described in Example 3($a$) may again be used, with a mixture of 27 g of the product of Example 2 and 67 g of the sodium salt of carbazole sulphonic acid replacing the 40 g of the former product used in Example 3($a$).

EXAMPLE 6

Preparation of an aqueous solution phosphorescent printing ink

An aqueous solution phosphorescent ink was prepared by the method described in Example 1 of British Patent Specification No. 1,494,102, using 8 g of the product of Example 2 above instead of 20 g of carbazole sulphonic acid sodium salt.

A two-component ink may be produced either by mixing two single-activator inks prepared in this manner, or by carrying out the preparation described above using 5.3 g of the product of Example 2 and 13 g of sodium carbazole-sulphonate.

EXAMPLE 7

Preparation of a paper-coating mix

A paper coating mix may be prepared by any of the methods described in Examples 2 to 4 of British Patent b Specification No. 1,411,102, if the 24 g of p-aminobenzoic acid used in those Examples are replaced either by 10 g of the free acid of the product of Example 2 or by a mixture of 16.6 g of carbazole sulphonic acid and 6.6 g of the free acid of the product of Example 2.

Similarly, the method of Example 6 of that specification may be used if the 30 g of p-aminobenzoic acid are replaced by either 12 f of the free acid of the product of Example 2 or by a mixture of 20 g of carbazole sulphonic acid and 8 g of the free acid of the product of Example 2.

EXAMPLE 8

Comparison of phosphorescence intensities

A series of phosphors was prepared by the method described in Example 3 but using the various activators numbered 1, 2 and 4 to 18 in the Table that follows. Samples of these phosphors, and a sample of the phosphor prepared in Example 3(a) (numbered 3 in the Table), were prepared in the form of 1/1000 inch drawdowns, and were irradiated with a long-wavelength ultraviolet light (365 nm), for a period of 200 ms. The mean intensity of the phosphorescent emission for each specimen was recorded under longwave UV excitation (365 nm) using a Post Office designed phosphorescence-measuring apparatus fitted with a blue-sensitive photo multiplier detector after a delay period of 150 ms. The relative after glow intensities (in arbitary units) are shown in the following Table I. It is clear that the intensity of emission of sulphonated p-aminobenzoyl naphthalene after long-wavelength irradiation is considerably higher than that of any of the other activators tested.

TABLE I

| | Phosphorescence Activator | Mean Brightness |
|---|---|---|
| 1. | Carbazole sulphonic acid | 48 |
| 2. | p-aminobenzophenone | 65 |
| 3. | Sulphonated p-aminobenzoyl naphthalene | 231 |
| 4. | p-hydroxy diphenyl sulphonic acid | 49 |
| 5. | Fluorene sulphonic acid | 3 |
| 6. | Diphenylene oxide sulphonic acid | 5 |
| 7. | 1-Naphthylamine 2-sulphonic acid | 29 |
| 8. | 2-Naphthylamine 5,9 Disulphonic acid (amino-J-acid) | 23 |
| 9. | α-Naphthoflavone | 100 |
| 10. | Vanillic acid (4-Hydroxy 3-methoxy benzoic acid) | 12 |
| 11. | 3-Hydroxy diphenylamine sulphonic acid | 25 |
| 12. | Diphenylamine | 2 |
| 13. | Diphenylguanidine | 17 |
| 14. | Acridone | 61 |
| 15. | 2-Aminobenzoflavone | 39 |
| 16. | Methyl umbelliferone | 40 |
| 17. | 2-Naphthylamine 6,8 Disulphonic acid (amino G-acid) | 12 |
| 18. | 2-Naphthol ε-sulphonic acid (Schaeffer's acid) | 7 |

EXAMPLE 9

A series of further compounds was prepared by a Friedel Crafts method from a polycyclic substrate compound and a corresponding acylation agent by the aforementioned Friedel Crafts method. Limited purification of the product obtained was carried out followed by chromatographic analysis and the product obtained (in most cases 90% pure) was incorporated in a urea formaldehyde pot melt in a concentration of 1% by weight. In each case, the phosphorescence colour was determined. The results obtained are set out in the foregoing Table II:

TABLE II

Table of Compounds Prepared

| Compound | Structure | Chromatography* | Phosphorescence in U/F Hot Melt |
|---|---|---|---|
| (1) 3-(4-amino benzoyl) phenanthrene | 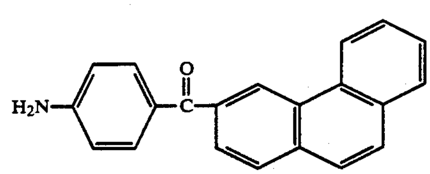 | main spot >90% | green very bright |
| (2) 3-(4-methoxy benzoyl) phenanthrene | 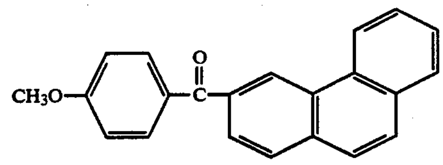 | main spot >90% | green very bright |
| (3) 3-Benzoyl phenanthrene | 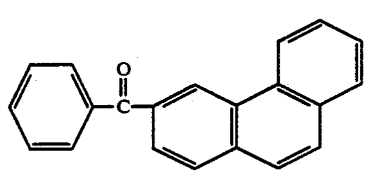 | main spot >90% | green bright |

TABLE II-continued
Table of Compounds Prepared

| Compound | Structure | Chromatography* | Phosphorescence in U/F Hot Melt |
|---|---|---|---|
| (4) 3-Acetyl phenanthrene | 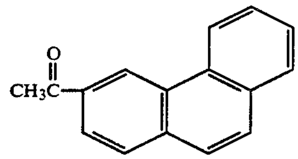 | main spot >90% | green not as bright as (3) |
| (5) 3-(2-Carboxy benzoyl) phenanthrene | 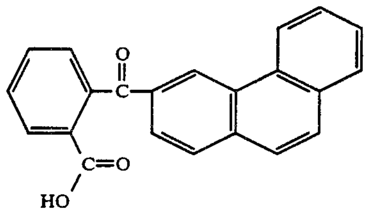 | main spot >90% | green very bright |
| (6) 3-(1-Carboxy naphth-8-oyl) phenanthrene | 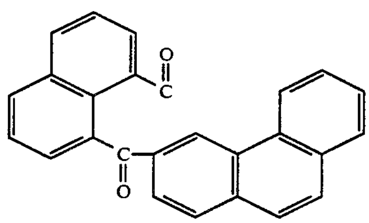 | mixture of products main spot ~50% of total | orange poor |
| (7) 3-(4-amino benzoyl) carbazole | 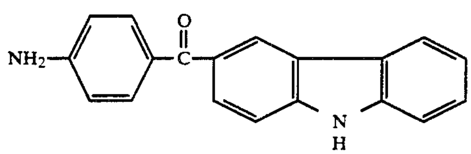 | unsuccessful separation in this system | blue green poor |

*Chromatography: TLC on silica gel using n-Hexane:Acetone 4:1 developer, visualized by fluorescence and UV absorption.

In general, it appears that 3-benzoyl phenanthrenes substituted in the 2 and 4 positions in the benzoyl group amino-methoxy or carboxylic acid groups give rise to very bright activators. b Compounds 1 to 4 are insoluble in aqueous solvents and would need to be sulphonated before use in aqueous inks. Sulphonation of compound 2 would have been difficult because of the lability of the methoxy group under strongly acidic conditions.

Experiments have shown that compound (5) is however the most satisfactory compound overall for the following reasons:

A. It has excellent characteristics as a phosphor activator.

B. It is soluble in aqueous solvents in the form of its sodium salt.

C. It does not contain an amino group attached to an aromatic hydrocarbon, thereby being acceptable on health and safety grounds.

D. It can be prepared at relatively low cost from low cost starting materials.

We claim:

1. An organic phosphor comprising a single phosphorescence activator in a matrix of a condensation resin that does not itself absorb ultra-violet or visible radiation at the excitation and emission frequencies of the phosphorescence activator, the single phosphorescence activator utilizing singlet-triplet transitions and being a compound of the general formula

$$(A)m-Ar-CO-X \qquad (I)$$

wherein Ar denotes a fused ring polycyclic aromatic group selected from the group consisting of: naphthyl, anthryl, phenanthryl, acenaphthyl and acenaphthenyl groups;

m is zero or an integer of from 1 up to the maximum number of ring positions in Ar available for subtitution;

X denotes a residue selected from the group consisting of: an alkyl group; a group of the formula (A)-m—Ar—; and, a group of the formula $(B)_n$Ph— wherein Ph is a phenyl group and n is zero or an integer of from 1 to 5; and A and B represent ring substituents selected from the group consisting of: alkyl, cycloalkyl, phenyl, alkoxy, cycloalkoxy, phenoxy, hydroxy, amino, hydrazino, amido, carboxyl, aldehyde, sulphonic acid, halogeno, cyano, azido and phenyl azo and substitution derivatives thereof; or an acid addition salt thereof when said compound is basic.

2. A phosphor as claimed in claim 1, wherein the single phosphorescence activator is 2-(4-amino-benzoyl) naphthalene.

3. A phosphor as claimed in claim 1, wherein the single phosphorescence activator is 3-(4-amino-benzoyl) phenanthrene.

4. A phosphor as claimed in claim 1 wherein the single phosphorescence activator is 2-(naphth-2-oyl)-naphthalene.

5. A phosphor as claimed in claim 1 wherein the single phosphorescence activator is 3-(4-aminobenzoyl)acenaphthylene.

6. A phosphor as claimed in claim 1 wherein the single phosphorescence activator is a compound or mixture of compounds of the formula:

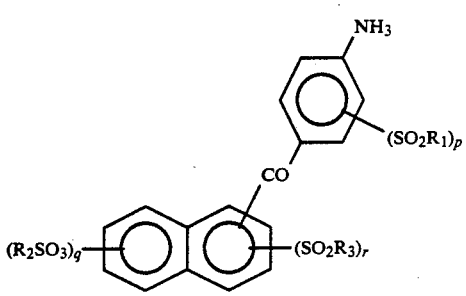

wherein:
each of $R_1$, $R_2$ and $R_3$ which may be the same or different represents
—OH
—OM wherein M represents a moiety selected from the group consisting of a monovalent cation, 1/m of an m-valent cation, a halogen atom, and
—OR wherein R represents a residue selected from the group consisting of substituted and unsubstituted alkyl, aryl and cycloalkyl radicals,
p represents zero or an integer from 1 to 4,
q represents zero or an integer from 1 to 4 and
r represents zero or an integer from 1 to 3 with the total of $p+q+r$ being at least 1.

7. A phosphor as claimed in claim 6, wherein the total of $p+q+r$ is 2.

8. A phosphor as claimed in claim 6, wherein the total of $p+q+r$ is 3.

9. A phosphor as claimed in claim 1, which contain as said single phosphorescence activator a compound or mixture of compounds having the formula:

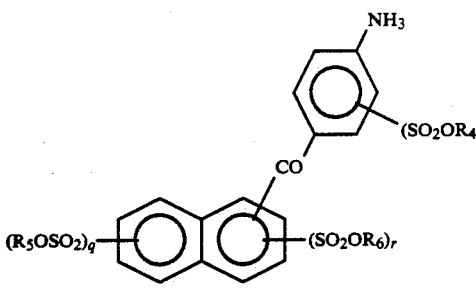

wherein each of $R_4$, $R_5$ and $R_6$ which may be the same or different represents a moiety selected from the group consisting of H and M, wherein M represents a moiety selected from the group consisting of: a monovalent cation; 1/m of an m-valent cation; and, a halogen atom; and,
p represents zero or an integer from 1 to 4,
q represents zero or an integer from 1 to 4 and
r represents zero or an integer from 1 to 3 with the total of $p+q+r$ being at least 1.

10. A phosphor as claimed in claim 9, wherein the total of $p+q+r$ is 2.

11. A phosphor as claimed in claim 9, wherein the total of $p+q+r$ is 3.

12. A phosphor as claimed in claim 1 which additionally includes a single phosphorescence activator which is carbazole sulphonic acid or a salt thereof.

13. A phosphor as claimed in claim 1, which additionally includes as a further phosphorescence activator carbazole sulphonic acid or a salt thereof, and, wherein said single phosphorescence activator and said further phosphorescence activator are present in a weight ratio within the range of from 0.2 to 1.0, based on the sodium salts of both activators.

14. A phosphor as claimed in claim 1, wherein the matrix comprises a condensation product of formaldehyde with an amine group-containing compound.

15. A phosphor as claimed in claim 14, wherein the amine compound is selected from the group consisting of urea and melamine.

16. A phosphor as claimed in claim 14, which contains a total of from 0.25 to 10 per cent by weight of said single phosphorescence activator, based on the total weight of the resin and the activator.

17. A precursor of an organic phosphor, which comprises an aqueous solution comprising as solute a single phosphorescence activator which utilizes singlet-triplet transitions and is a water soluble compound of the general formula $$(A)_m—Ar—CO—X \qquad (I)$$

wherein Ar denotes a fused ring polycyclic aromatic group selected from the group consisting of: naphthyl, anthryl, phenanthryl, acenaphthyl and acenaphthenyl groups;
m is zero or an integer of from 1 up to the maximum number of ring positions in Ar available for substitution;
X denotes a residue selected from the group consisting of: an alkyl group; a group of the formula (A)-m—Ar—; and, a group of the formula $(B)_n$Ph— wherein Ph is a phenyl group and n is zero or an integer of from 1 to 5; and
A and B represent ring substituents selected from the group consisting of: alkyl, cycloalkyl, phenyl, alkoxy, cycloalkoxy, phenoxy, hydroxy, amino, hydrazino, amido, carboxyl, aldehyde, sulphonic acid, halogeno, cyano, azido and phenyl azo and substitution derivatives thereof; or an acid addition salt thereof when said compound is basic, and further comprising as solute a soluble precondensate obtained by a reaction between two or more components, the soluble precondensate being capable of further reaction in the absence of the single phosphorescence activator to form an insoluble condensation product that does not substantially absorb ultraviolet radiation at any wavelength at which the single phosphorescence activator substantially absorbs ultraviolet radiation and being capable of such further reaction in the presence of the single phosphorescence activator to form a phosphorescent insoluble condensation product.

18. A phosphor precursor as claimed in claim 17, wherein the single phosphorescence activator is 2-(4-aminobenzoyl) naphthalene.

19. A phosphor precursor as claimed in claim 17, wherein the single phosphorescence activator is 3-(4-aminobenzoyl) phenanthrene.

20. A phosphor precursor as claimed in claim 17, wherein the single phosphorescence activator is 2-(naphth-2-oly)-naphthalene.

21. A phosphor precursor as claimed in claim 17, wherein the single phosphorescence activator is 3-(4-aminobenzoyl)acenaphthylene.

22. A phosphor precursor as claimed in claim 17, wherein the single phosphorescence activator is a compound or mixture of compounds of the formula:

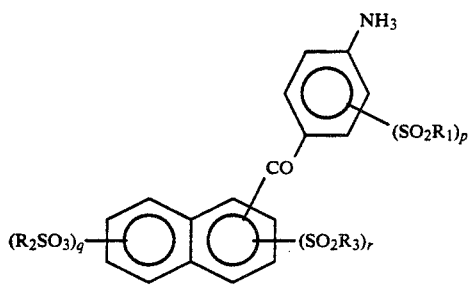

wherein:
each of $R_1$, $R_2$ and $R_3$ which may be the same or different represents
—OH
—OM wherein M represents a moiety selected from the group consisting of a monovalent cation, 1/m of an m-valent cation, a halogen atom, and
—OR wherein R represents a residue selected from the group consisting of substituted and unsubstituted alkyl, aryl and cycloalkyl radicals,
p represents zero or an integer from 1 to 4,
q represents zero or an integer from 1 to 4 and
r represents zero or an integer from 1 to 3 with the total of p+q+r being at least 1.

23. A phosphor precursor as claimed in claim 22, wherein the total of p+q+r is 2.

24. A phosphor precursor as claimed in claim 22, wherein the total of p+q+r is 3.

25. A phosphor precursor as claimed in claim 17, which contains as said single phosphorescence activator a compound or mixture of compounds having the formula:

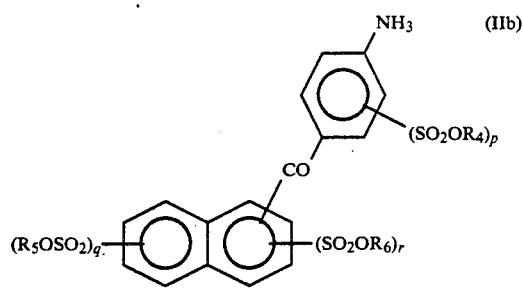

wherein each of $R_4$, $R_5$ and $R_6$ which may be the same or different represents a moiety selected from the group consisting of H and M, wherein M represents a moiety selected from the group consisting of: a monovalent cation; 1/m of an m-valent cation; and, a halogen atom; and,
p represents zero or an integer from 1 to 4,
q represents zero or an integer from 1 to 4 and
r represents zero or an integer from 1 to 3 with the total of p+q+r being at least 1.

26. A phosphor precursor as claimed in claim 25, wherein the total of p+q+r is 2.

27. A phosphor precursor as claimed in claim 25, wherein the total of p+q+r is 3.

28. A phosphor precursor as claimed in claim 17, which additionally includes as a further phosphorescence activator carbazole sulphonic acid or a salt thereof.

29. A phosphor as claimed in claim 17, which additionally includes as a further phosphorescence activator carbazole sulphonic acid or a salt thereof, and, wherein said single water-soluble phosphorescence activator and said further phosphorescence activator are present in a weight ratio within the range of from 0.2 to 1.0, based on the sodium salts of both activators.

* * * * *

UNITED STATES PATENT AND TRADEMARK OFFICE
CERTIFICATE OF CORRECTION

PATENT NO. : 5,100,580

DATED : March 31, 1992

INVENTOR(S) : Powell et al.

Page 1 of 2

It is certified that error appears in the above-indentified patent and that said Letters Patent is hereby corrected as shown below:

At Column 2, line 8, please delete "amino" and insert therefor –amido– and at line 59, please delete "tor" and insert therefor –for–.

At Column 3, line 47, after "Ia", please delete the formula and insert the following formula.

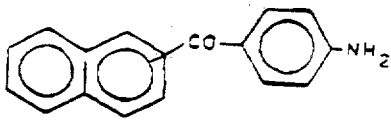

–; and at line 59, please delete "NH," and insert therefor –NH$_2$–.

UNITED STATES PATENT AND TRADEMARK OFFICE
CERTIFICATE OF CORRECTION

PATENT NO. : 5,100,580

DATED : March 31, 1992

INVENTOR(S) : Powell et al.

It is certified that error appears in the above-indentified patent and that said Letters Patent is hereby corrected as shown below:

At Column 4, line 14, after "Ar", please insert -,-.

At Column 7, line 49, please delete "or one" and insert therefor -of the-.

At Column 8, line 42, please delete "alterative" and insert therefor -alternative-.

At Column 9, line 6, please delete "b"; and please delete "1,411,102" and insert therefor -1,491.102- and at line 11, please delete "B" and insert -5-.

At Column 11, line 13, after $\overset{O}{\underset{C}{\|}}$ , please insert -OH- and at line 43, please delete -b-.

Col. 13
At Claim 9 line 45, please delete "NH," and insert therefor -NH$_2$-.

Col. 15
At Claim 22, line 11, please delete "NH," and insert therefor -NH$_2$-.

Col. 16
At Claim 25, line 5, please delete "NH," and insert therefor -NH$_2$-.

Signed and Sealed this

Fifteenth Day of August, 1995

BRUCE LEHMAN

*Attest:*

*Attesting Officer*     *Commissioner of Patents and Trademarks*